United States Patent [19]

Meyer et al.

[11] Patent Number: 4,531,965
[45] Date of Patent: Jul. 30, 1985

[54] WEED CONTROL METHOD AND COMPOSITION

[75] Inventors: Jacques Meyer, Zofingen; Walter Schären, Vordemwald, both of Switzerland

[73] Assignee: Siegfried Aktiengesellschaft, Zofingen, Switzerland

[21] Appl. No.: 443,373

[22] Filed: Nov. 22, 1982

[30] Foreign Application Priority Data

Nov. 7, 1981 [CH] Switzerland .......................... 7595/81

[51] Int. Cl.$^3$ .............................................. A01N 43/54
[52] U.S. Cl. ............................................. 71/92; 71/108
[58] Field of Search .................................... 71/92, 108

[56] References Cited

U.S. PATENT DOCUMENTS 3,036,357  2/1966  Loux ........................................ 71/92
3,652,645  3/1972  Theissen ................................. 71/118

Primary Examiner—Catherine L. Mills
Attorney, Agent, or Firm—Werner W. Kleeman

[57] ABSTRACT

A method of selectively controlling weeds in crop areas, notably vineyards or fruit plantations, by applying a composition that includes different active herbicidal ingredients; the composition comprises a synergistic combination of about 1 part, by weight, of methyl-5-(2,4-dichlorophenoxy)-2-nitrobenzoate as a first active ingredient, and about 1 to 5 parts, by weight, of 3-tert.butyl-5-chloro-6-methyl-uracil as a second active ingredient.

The novel composition comprises said synergistic combination and may further contain a mineral oil and adjuvants such as an emulsifier.

5 Claims, No Drawings

WEED CONTROL METHOD AND COMPOSITION

CROSS-REFERENCE TO RELATED CASES

This application generally relates to subject matter disclosed in our commonly assigned U.S. application Ser. No. 06/345,490 filed Feb. 3, 1982, as well as to subject matter disclosed in our commonly assigned U.S. application Ser. No. 227,085 filed Jan. 16, 1981, and U.S. application Ser. No. 850,468 filed Nov. 10, 1977, issued as U.S. Pat. No. 4,211,551 on July 8, 1980.

BACKGROUND OF THE INVENTION (a) Field of the Invention

The present invention relates to weed control by means of herbicides and more particularly to methods and compositions for selectively controlling weeds in crop areas such as vineyards and fruit plantations.

(b) Description of the Prior Art

Weed control for agricultural purposes remains a topic of great importance even though many different classes of compounds as well as thousands of specific compounds have been disclosed in the literature for the purposes of both general and selective weed control.

However, spontaneous growth of undesired plants or weeds in a crop area that should be maintained free of such weeds for optimum yield is an extremely complex phenomenon dependent upon various static and dynamic factors including type of soil, climate, floral area, adventive plant ingressions, etc. and no generally applicable or universal solution of the problems involved in recurring or spontaneous growth of weeds by agrochemical means is expected in the near future.

Other unsolved problems in this area include widely differing sensitivities of crop plants against herbicidal chemicals as well as the fact that repression of one weed species may cause increased growth of another competing weed species, and that some weeds tend to become resistant against previously effective herbicides.

Thus, there is a continued need for novel and improved weed control methods and compositions while, at the same time, introduction of completely new chemicals causes problems because of the need of long-term testing for such properties as general environmental effects, residue, chronic toxicity, teratogenicity, etc. The use of specific combinations of known and well-tested substances would reduce these problems if the ingredients of the combination complement each other as is the case, typically, for combinations of herbicidal substances with surfactants or the like adjuvants.

The results of combining different herbicidal chemicals generally called active ingredients are not, as a rule, predictable. In theory, suitably complemental active ingredients might yield mixtures wherein the properties of the mixture should be predictable from the properties of the herbicidal ingredients. In practice, however, any mixture of two or more herbicidal active ingredients entails the risk of an unexpected reinforcement of negative properties, e.g. damage to crop plants, and even a merely additive, i.e. favorably complemental mixture of active ingredients is considered a "lucky" mixture in the art and is not predictable.

The most desirable aim is, of course, a combination having properties that are more advantageous than the sum of the properties of the active ingredients, i.e. a better-than-additive or so-called synergistic combination.

Specifically, a continued need exists for improved herbicide control in vineyards and other fruit-type croplands with relatively large (in relation to weeds) crop plants and/or large free areas between the crop plants or crop plant rows such that a major surface portion of the soil area is and remains freely exposed to weed growth; in such exposed areas, a particularly broad variety or spectrum of different types of weeds tends to flourish, e.g. including dicotylodone-type or broad-leaf weeds as well as monocotylodone-type grass weeds comprising both annual and perennial types. Thus, an exceptionally wide spectrum of herbicidal activities must be combined with avoidance of damage to crop plants in weed control of vineyards and fruit plantations while, at the same time, a satisfactory permanence of weed control should be combined with absence of detrimental effects upon the soil, the herbicide-applying personnel and consumers of the crops. Prior art methods and compositions fail to achieve this satisfactorily.

Accordingly, it is a primary object of the invention to provide for an improved method of weed control in vineyards and fruit plantations.

Another important object is to provide for a novel combination of previously known herbicidal chemicals for improved weed control in vineyards and fruit plantations.

Further objects will become apparent as this specification proceeds.

In the course of the research leading to the present invention, it was observed that the herbicidal effectiveness of binuclear phenoxy compounds and specifically the methyl ester of 5-(2,4-dichlorophenoxy)-2-nitrobenzoic acid having the structural formula

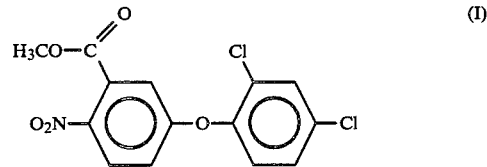

could be substantially improved if combined with another type of active ingredient discussed more fully below.

It is to be noted that the formula (I) compound or first active ingredient of the combination according to the invention is a prior art herbicide that has been known and tested for many years. The formula (I) compound is disclosed, inter alia, in U.S. Pat. No. 3,652,645 (incorporated herein by way of reference) and is commercially available; its physical, toxicological and environmental properties have been well researched and a wealth of information about this chemical will be provided by any commercial producer of that substance.

However, while the formula (I) compound is known to be a herbicide that is suitable for various purposes, it has not been satisfactory for use in such crops as grapes, apples and other commercially important fruits, notably in view of the relatively restricted effectiveness range both with regard to weed species as well as with regard to sufficient permanence.

A number of combinations of the formula (I) compound with other active ingredients has been suggested in the art, cf. Swiss Pat. No. 578,319, for pre-emergence weed control, i.e. a method not generally suitable in vineyards or fruit plantations.

Now, it has been found according to the invention that substantial and surprising advantages will be obtained when using the formula (I) compound in combination with another prior art herbicide, i.e. 3-tert.butyl-5-chloro-6-methyluracil, having the structural formula (II)

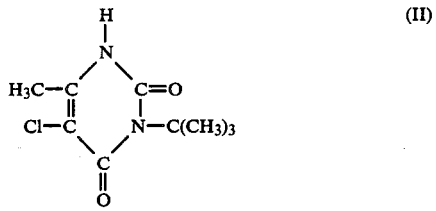

for controlling weeds in crop areas of the type indicated above, i.e. in vineyards or fruit plantations, e.g. crop areas of grapes, apples, berry-fruit and similar crop plants that favor development of heavily populated weed growth areas.

The formula (II) compound is disclosed, inter alia, in U.S. Pat. No. 3,235,357 (incorporated herein by reference) as a herbicide and is available commercially. Again, because of extended long-term use of the formula (II) compound its physical, chemical, biological and environmental properties have been carefully reviewed and such data are available from suppliers of the commercial products.

The novel combination of the formula (I) compound and the formula (II) compound according to the invention contains about 1 to about 5 parts and preferably about 1 to 2 parts, by weight, of the formula (II) compound per each part, by weight, of the formula (I) compound. In other words, the ratio (I):(II) is between about 1 and about 0.2.

When the ratio of ingredient (I) to ingredient (II) is substantially above 1 (e.g. two parts of (I) per each part of (II)) there will be less or no synergism of the ingredients. On the other hand, i.e. with a (I):(II) ratio of substantially below 0.2 (e.g. ten parts of (II) per one part of (I)), both the synergistic effects as well as the overall effectiveness tend to become impaired.

In general, the combination of (I)+(II) will be effective in amounts or dosages of about 2 kg to about 5 kg, preferably about 3.5 to 4 kg, of (I)+(II) per hectare of crop area, i.e. 1.5 to 3.8 pounds/acre or preferably 2.6 to 3 pounds per acre. Preferably, the portions of (I) and (II) in the combination is such that about 2 kg to about 2.8 kg of ingredient (II) will be applied per hectare (1.5 to 2.1 pounds/acre) of crop area.

Both ingredients (I) and (II) can be used herein in commercially available grades and in conventional particle sizes for herbicide use of typically below 30 μm, notably 10 μm or smaller.

At a dosage of substantially below about 2 kg of (I)+(II) per hectare, total effectiveness of weed control—notably against well-developed weed plants—may suffer while at dosages of substantially above about 5 kg of (I)+(II) per hectare commercially significant advantages tend to become too small.

Both active ingredients (I) and (II) of the subject combination are normally solid and can be applied onto a crop area in solid form, e.g. as a pulverulent or granular preparation generally in mixture with a solid extender or diluent. Alternatively, the ingredients can be dispersed or dissolved in a liquid extender or diluent.

Suitable solid or liquid extenders are known in the art and include finely divided solids such as talcs, clays, kieselgur, nut-shell flower as well as aqueous and non-aqueous liquids.

Generally speaking, a composition for use in the invention may contain from about 1% to about 99%, by weight, of the combination (I)+(II) depending upon the type of application as well as the applicators used. As representative examples tank applicators and tank mixtures or dusting equipment and dust mixtures can be mentioned. As is conventional, tank mixtures can be made from relatively concentrated compositions and mixed with water prior to application.

For example, a wettable powder may contain up to 50 or 60%, by weight, of active ingredients (I)+(II) while a granulate may include as little as 3 to 10%, by weight, of the active ingredients.

The effectiveness of the inventive combination (I)+(II) may be increased advantageously, notably near the lower end of the above mentioned range of effective amounts, by using the synergistic combination together with a mineral oil such as "white oil" or a similar substantially non-volatile refined petroleum fraction of the type conventionally used in agrochemistry; essentially paraffinic hydrocarbon oils are preferred and numerous products including "white oil" are available commercially as essentially inert spray oils. Examples and parameters of mineral oils suitable for the invention are given, for example, in the "Pesticide Manual" (edited by H. Martin and C. R. Worthing, issued by the British Crop Protection Council, 4th edition [1974], page 397). Suitable mineral oils will boil, under normal pressure, at temperatures of above 200° C., preferably above 250° C., e.g. at 300° C. or more. A specific example of a suitable oil for use herein is the commercial product "Spray Oil 11E" obtainable from the Sun Oil Company.

When applying the synergistic combination of (I) and (II) together with a mineral oil onto a crop area good results will generally be obtained with a composition that contains such mineral oil in an amount of about 30% to about 300%, by weight, based upon the weight of ingredient (I). For example, a suitable mixture of (I) and (II) plus mineral oil will be obtained by using about 1 Liter to about 3.5 Liters of mineral oil per each Kilogram of the synergistic combination (I)+(II).

When applying the novel combination of ingredients (I)+(II) according to the invention together with a mineral oil of the type explained above, it is preferred to use at least one adjuvant which is an emulsifying agent for the mineral oil in the weed control composition. Suitable emulsifiers for agrochemical use are known and emulsifiers of various categories that are available commercially can be used herein, e.g. alcanol amines of fatty acids, polyglycol ethers and the like; numerous other examples will be found in standard reference books, e.g. "McCutcheon's Detergent and Emulsifier Annual" or "Encyclopedia of Surface-Active Agents" by Sisley and Wood. A specific example is "Atlox 4853 B" obtainable from Atlas Chemical Industries N.V.

Further, compositions according to the invention may include conventional further additives, adjuvants and the like constituents depending upon the formulation and the intended type of use of the inventive composition. Again, such additives are known in the agrochemical art and include thickening agents, defoaming agents, adhesion-improving agents, dispersing agents, anti-freeze agents, coloring materials, etc. Selection may depend upon the type of formulation, e.g. concentrate or spray.

Inventive compositions can be obtained by conventional blending, mixing or emulsifying methods from the above constituents, including milling in hammer mills, high-shear mixers, fluid mills and the like.

Suitable types of preparations for application of the inventive combination according to the invention include wettable powders, suspension concentrates of the flowable type as well as granulates and the like, and concentration of the active ingredients may vary.

The invention will now be explained in more detail in the following examples that illustrate, but are not intended to limit, the invention.

Parts and percentages are by weight unless otherwise indicated. Field tests were made at various trial sites in Switzerland (Roggwil, TG; Bürglen, TG; Zofingen, AG; Wilchingen, SH; Hüntwangen, ZH). A total of six replicated trials (two in apples, four in grapes) was made at each site and each site contained a plurality of defined plots of at least about 10 m² each. There was at least one untreated plot per site as control and one or more plots for comparative purposes.

The compositions tested were applied between April and June by one-time spraying of the post-emergent weeds and by repeated observation of the trial sites for a period of three months (grapes) and four months (apples) at intervals of four weeks. Weed control effectiveness (for defined weed species) was made by visual scoring according to the scale of evaluation defined by the European Weed Research Council; this EWRC-scale ranges from 1 to 9 in which "9" indicates "no damage of weed", i.e. a weed control effectiveness of Zero percent, while "1" indicated total killing of the weeds concerned, i.e. a weed control effectiveness of 100%.

The compositions were applied in various dosages in the form of aqueous sprays, however at a substantially uniform spray rate of about 1000 Liters per hectare with a field plot sprayer ("Van der Weij") using a pressure of 3 bar.

EXAMPLES (1) Preparation of Compositions (A) A wettable powder composition according to the invention was prepared from 25.1 parts of compound (I) (commercial grade, 97%), 37.5 parts of compound (II) (commercial grade, 80%), 10 parts of commercial lignin sulfonate, 5 parts of finely divided silica, 2 parts of the commercial alkylaryl sulfonate surfactant sold under the trade name "NEKAL" (reg. trademark) by BASF and 20.4 parts of white bolus powder (white bole or kaolin).

After preparing, pregrinding and sieving a blend of compounds (I) and (II), the other constituents emunerated above were added to the blend and processed by passage through a jet mill. The product was a flowable powder.

Generally, such as wettable powder is suitable for dispersion in water at a proportion of 20 to 600 parts of water per part of the composition to provide aqueous compositions that can be applied at a spray rate of between 500 to 1500 Liters per hectare.

In practice, amounts of the wettable powder between 2.5 kg/ha and 10 kg/ha, preferably between 6 to 8 kg/ha, have been found to be particularly effective.

(B) Wettable powders were made in the manner explained above except that the portions of the active ingredients (I) and (II) were changed so as to provide for further compositions according to the invention as well as for comparative compositions.

Comparative substances or compositions used in the tests and believed to be representative of the best prior art weed control agents for use in vineyards and fruit plantations were:

(a) Glyphosate (trade name "ROUNDUP"),
(b) composite weed control agent made of Simazin, Diquat, Paraquat and Ajutol.

(2) General Evaluation (A) When comparing the weed control effects obtained with the inventive composition with the effects obtained with Glyphosate it was found that (a) the inventive composition is effective against a broader spectrum of weed species extending from dicotylodones to grass-type weeds and Carex species including annual as well as perennial species, and (b) that permanence of weed control was significantly prolonged.

Specifically, comparative field trials in apple plantations and vineyards by a single post-emergence treatment with Glyphosate (2.46 kg a.i./ha) to test long-term effectiveness against Agropyron sp., Carex sp. and Poa sp. resulted in an average EWRC value of 6.6 upon observation four months after the treatment while the inventive composition (1.1 kg a.i. of (I)/ha and 2.4 kg a.i. of (II)/ha) resulted in an EWRC value of 1.8 under the same conditions.

(B) An analogous evaluation of the effectiveness against Cirsium arvense, Stellaria media, Taraxacum officinale and Veronica hederifolia three months after post-emergence treatment resulted in an EWRC average value of 3 for Glyphosate, on the one hand, and an EWRC average value of 1 for the inventive combination (I)+(II), on the other hand.

(3) Advantage of (I)+(II) Ingredient Combination over (I), (II) Ingredients per se (A) Resorption Route The results of field tests made so far support the conclusion that the inventive combination of the ingredients (I)+(II) provides the advantage that it is resorbed by the weeds both via the roots as well as via the leaves.

(B) Synergism

The inventive combination of ingredients (I)+(II) shows a clearly super-additive complementation of effects over those of the individual ingredients (I), (II) applied separately.

The results of several representative tests are enumerated below in Tables 1 and 2, again in terms of average EWRC values obtained four months after a single post-emergence treatment.

TABLE 1

| Results of Field Trials of Weed Control Effectiveness against certain Weed Species | | | |
|---|---|---|---|
| Weed species | active ingredient | dosage (kg/ha) | average EWRC value |
| Agropyron repens | (I) | 2.2 | 9 |
| Agropyron repens | (II) | 2.4 | 3 |
| Agropyron repens | (I) + (II) | 1.1/2.4 | 1.5 |
| Poa annua | (I) | 1.1 | 9 |
| Poa annua | (II) | 1.2 | 4 |
| Poa annua | (I) + (II) | 1.1/1.2 | 2 |
| Carex sp. | (I) | 2.2 | 5 |
| Carex sp. | (II) | 2.4 | 4.5 |
| Carex sp. | (I) + (II) | 2.2/2.4 | 1 |
| Convolvulus arvensis | (I) | 2.2 | 4.5 |
| Convolvulus arvensis | (II) | 2.4 | 7 |
| Convolvulus | (I) + (II) | 2.2/2.4 | 3 |

TABLE 1-continued
Results of Field Trials of Weed Control
Effectiveness against certain Weed Species

| Weed species | active ingredient | dosage (kg/ha) | average EWRC value |
|---|---|---|---|
| arvensis | | | |

TABLE 2
Effectiveness of Inventive Combination compared with Individual Components and Prior Art Products

| Active ingredient | dosage (kg/ha) | Agropyron repens | Poa annua | Poa trinalis | Carex sp. | Convolvulus arvensis | Equisetum arvense | Taraxacum officinalis |
|---|---|---|---|---|---|---|---|---|
| (I) + (II) (invention) | 1.25/1.5 | 2 | 1 | 1 | 4.5 | 3 | 4 | 2 |
| (I) + (II) (invention) | 1.75/2.1 | 1.5 | 1 | 1 | 2.5 | 3 | 4 | 1 |
| (I) + (II) (invention) | 2.5/3.0 | 1 | 1 | 1 | 1.5 | 2 | 3.5 | 1 |
| (II) (80%) | 1.5 | 3.5 | 2 | 1 | 7.5 | 8.5 | 5.5 | 6.5 |
| (comparative) | 2.1 | 2 | 1 | 1 | 6 | 2.5 | 3.5 | 2.5 |
| (I) (440 g/l) | 1.25 | 9 | 9 | 9 | 6.5 | 5.5 | 7.5 | 6.5 |
| (comparative) | 1.75 | 9 | 9 | 9 | 4 | 2 | 5.5 | 2.5 |
| "ROUNDUP" | 3.28 | 2 | 5 | 1.5 | 4.5 | 3 | 9 | 5 |
| (comparative) | 4.1 | 1.5 | 4 | 1 | 2 | 4 | 7 | 5 |
| Simazin + Diquat + Paraquat + Ajutol (comparative) | 2.5 / 0.99 / 0.5 / (not act.) | 4 | 1 | 1 | 7 | 9 | 7 | 2 |
| Control (untreated) | | 9 | 9 | 9 | 9 | 9 | 9 | 9 |

Evaluation: 4 months after treatment
Scale: 1-9 EWRC
1 = 100% Effectiveness
9 = 0% Effectiveness The advantages of the present invention, as well as changes and modifications of the disclosed embodiments thereof, will be apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. In the method of controlling a broad spectrum of weeds in a vineyard or fruit plantation, by applying thereto in a post-emergence treatment an effective amount of a selectively herbicidal composition comprising different active herbicidal ingredients; the improvement consisting essentially of applying said composition in a single effective treatment by one-time spraying of said vineyard or fruit plantation after emergence of said weeds, said composition comprising a combination of methyl-5-(2,4-dichlorophenoxy)-2-nitrobenzoate as a first active ingredient (I) admixed with 3-tert.butyl-5-chloro-6-methyl-uracil as a second active ingredient (II); said combination containing about 1 to about 5 parts, by weight, of said second active ingredient (II) per each part, by weight, of said first active ingredient (I).

2. The method of claim 1 wherein said composition contains about 1 to about 2 parts, by weight, of said second active ingredient (II) per each part, by weight, of said first active ingredient (I).

3. The method of claim 1 or 2 wherein said composition is applied onto said vineyard or fruit plantation in an amount sufficient to provide about 2 kg to about 5 kg of said combination per each hectare of said vineyard or fruit plantation.

4. The method of claim 3 wherein said composition is applied onto said vineyard or fruit plantation in an amount sufficient to provide about 3.5 kg to about 4.5 kg of said combination, said mixture being composed to provide said second ingredient (II) in an amount of about 2 kg to about 2.8 kg per hectare of said vineyard or fruit plantation.

5. The method of claim 1 wherein said combination is applied in admixture with a mineral oil, said admixture containing about 1 liter to about 3.5 liters of said mineral oil per each kilogram of said combination.

* * * * *